(12) United States Patent
Menassa et al.

(10) Patent No.: US 9,067,020 B2
(45) Date of Patent: Jun. 30, 2015

(54) NEEDLELESS INJECTOR WAND ASSEMBLY (76) Inventors: Karim Menassa, Montreal (CA);
Maurice Menassa, Pierrefonds (CA);
Adam Gadoua, Laval (CA)

(*) Notice: Subject to any disclaimer, the term of this patent is extended or adjusted under 35 U.S.C. 154(b) by 0 days.

(21) Appl. No.: 13/261,753

(22) PCT Filed: Apr. 3, 2012

(86) PCT No.: PCT/CA2012/000286
§ 371 (c)(1),
(2), (4) Date: Oct. 1, 2013

(87) PCT Pub. No.: WO2012/135938
PCT Pub. Date: Oct. 11, 2012

(65) Prior Publication Data
US 2014/0023985 A1  Jan. 23, 2014

Related U.S. Application Data (60) Provisional application No. 61/457,462, filed on Apr. 4, 2011.

(51) Int. Cl.
*A61M 5/30* (2006.01)
*A61M 5/155* (2006.01)
*A61M 5/20* (2006.01)
*A61M 5/31* (2006.01)

(52) U.S. Cl.
CPC ............... *A61M 5/30* (2013.01); *A61M 5/155* (2013.01); *A61M 5/204* (2013.01); *A61M 5/2053* (2013.01); *A61M 2005/3128* (2013.01); *A61M 2209/01* (2013.01)

(58) Field of Classification Search
CPC ....... A61M 5/30; A61M 5/204; A61M 5/2053; A61M 2005/3128; A61M 2209/01; A61M 5/155
USPC ............. 604/68–72, 140–141, 145–148, 181, 604/183, 236, 238, 104
See application file for complete search history.

(56) References Cited

U.S. PATENT DOCUMENTS

| 3,292,622 | A  | * | 12/1966 | Banker ........................... 604/70 |
| 5,891,085 | A  | * | 4/1999  | Lilley et al. ..................... 604/68 |
| 6,290,690 | B1 | * | 9/2001  | Huculak et al. ............... 604/521 |
| 7,357,781 | B2 | * | 4/2008  | Menassa ......................... 604/70 |
| 2008/0103564 | A1 | * | 5/2008 | Burkinshaw et al. ........... 607/96 |

* cited by examiner

Primary Examiner — Bhisma Mehta
Assistant Examiner — William Frehe
(74) Attorney, Agent, or Firm — George A. Seaby (57) ABSTRACT

A needleless injector syringe includes a tubular barrel containing a first chamber for receiving a liquid, a nozzle on a front end of the barrel, a piston which drives a plunger for discharging the liquid through the nozzle, a second chamber in which the piston slides, a third chamber in fluid communication with the second chamber for receiving gas from said second chamber during forward movement of the piston, and for carrying gas to the second chamber to cause the piston to retract, and a breach plug closing a rear end of the barrel for directing gas under pressure alternately against the rear end of the piston and to the third chamber for driving the piston between the discharge position and a retracted position.

5 Claims, 11 Drawing Sheets

NEEDLELESS INJECTOR WAND ASSEMBLY

This application claims the benefit of Provisional Application Ser. No. 61/457,462, filed Apr. 4, 2011, and titled "NEEDLELESS INJECTOR WAND ASSEMBLY".

BACKGROUND OF THE INVENTION

This invention relates to a needleless injector and in particular to a needleless injector wand assembly.

U.S. Pat. No. 7,357,781, issued to Karim Menassa on Apr. 15, 2008, discloses a needleless injector in the shape of a pistol. The patented injector includes a barrel for receiving a liquid, a nozzle containing an injection orifice closing one end of the barrel, a plunger in the barrel, a piston for driving the plunger towards the nozzle end of the barrel, a magnet assembly for retaining the piston in a rest position, and a trigger connected to a valve for admitting gas under pressure to drive the magnet assembly forwardly against the plunger. While the above described injector has proven to be effective for its intended purpose, i.e., the carrying out of successive injections quickly, the apparatus is somewhat bulky and is not designed for use in confined areas such as the mouth when doing dental work. Moreover, when doing dental work or when an injection is to be made to the face or neck, a person receiving the injection would find a small injector less intimidating than a large gun-shaped apparatus.

SUMMARY OF THE INVENTION

The object of the present invention is to provide a relatively simple needleless injector in the form of a small wand assembly which can be used in confined areas.

Accordingly, the invention provides an injector wand assembly including a tubular barrel containing a plunger and a piston assembly, which is operated by a gas under pressure, the gas being introduced and discharged from one end of the barrel, and a drug or other liquid being discharged through a disposable nozzle on the other end of the barrel.

More specifically, the invention provides a needleless injector wand assembly comprising a tubular barrel; a first chamber at a front, discharge end of said barrel for receiving an injectable liquid from a source thereof; a nozzle on the front end of said barrel for discharging liquid from the first chamber; a plunger slidable in the barrel for movement between a retracted position in which liquid is drawn into the first chamber and an extended position in which the liquid is discharged through said nozzle; a second chamber in said barrel rearwardly of and separated from said first chamber; a piston slidable in said second chamber for movement under fluid pressure between an extended position in which it moves the plunger to the extended position and a retracted position; a third chamber in said barrel for alternately receiving gas under pressure from said second chamber during movement of the piston from the retracted to the extended position, and for introducing the gas under pressure to said second chamber during movement of said piston from the extended to the retracted position; a breach plug closing a rear end of said barrel including a first passage for carrying a gas under pressure to a rear end of the piston to cause the piston to move from the retracted to the extended position, and a second passage for carrying the gas under pressure to and from said third chamber to cause said piston to alternately move from the retracted to the extended position and from the extended to the retracted position.

BRIEF DESCRIPTION OF THE DRAWINGS

The invention is described in greater detail hereinafter with reference to the accompanying drawings, which illustrate a preferred embodiment of the invention, and wherein.

It should be noted that through the description the "front end" is the discharge end of the wand.

DETAILED DESCRIPTION OF THE DRAWINGS

Figure 1:
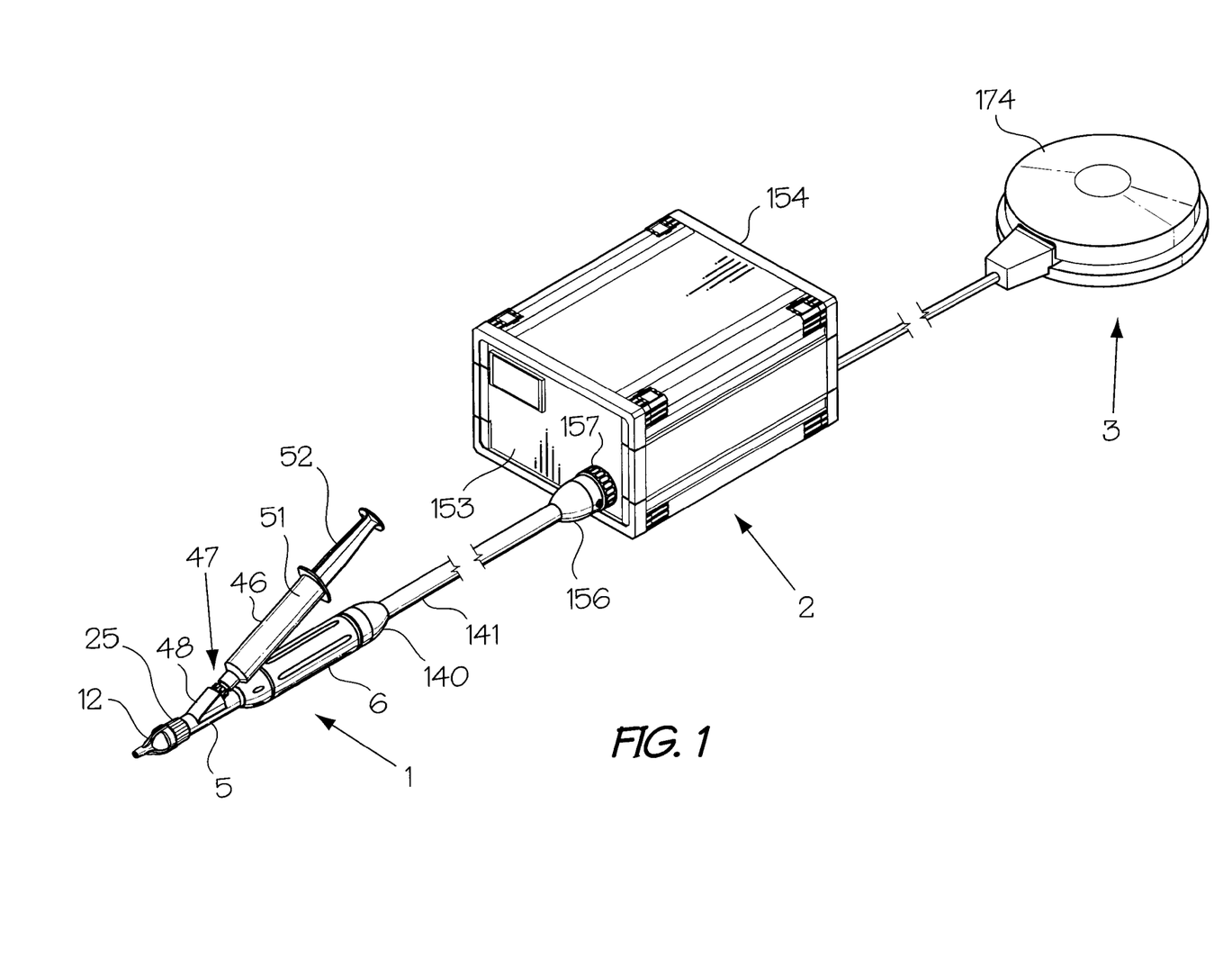
FIG. 1 is an isometric view of a needleless injector wand assembly in accordance with the invention.
Figure 2:
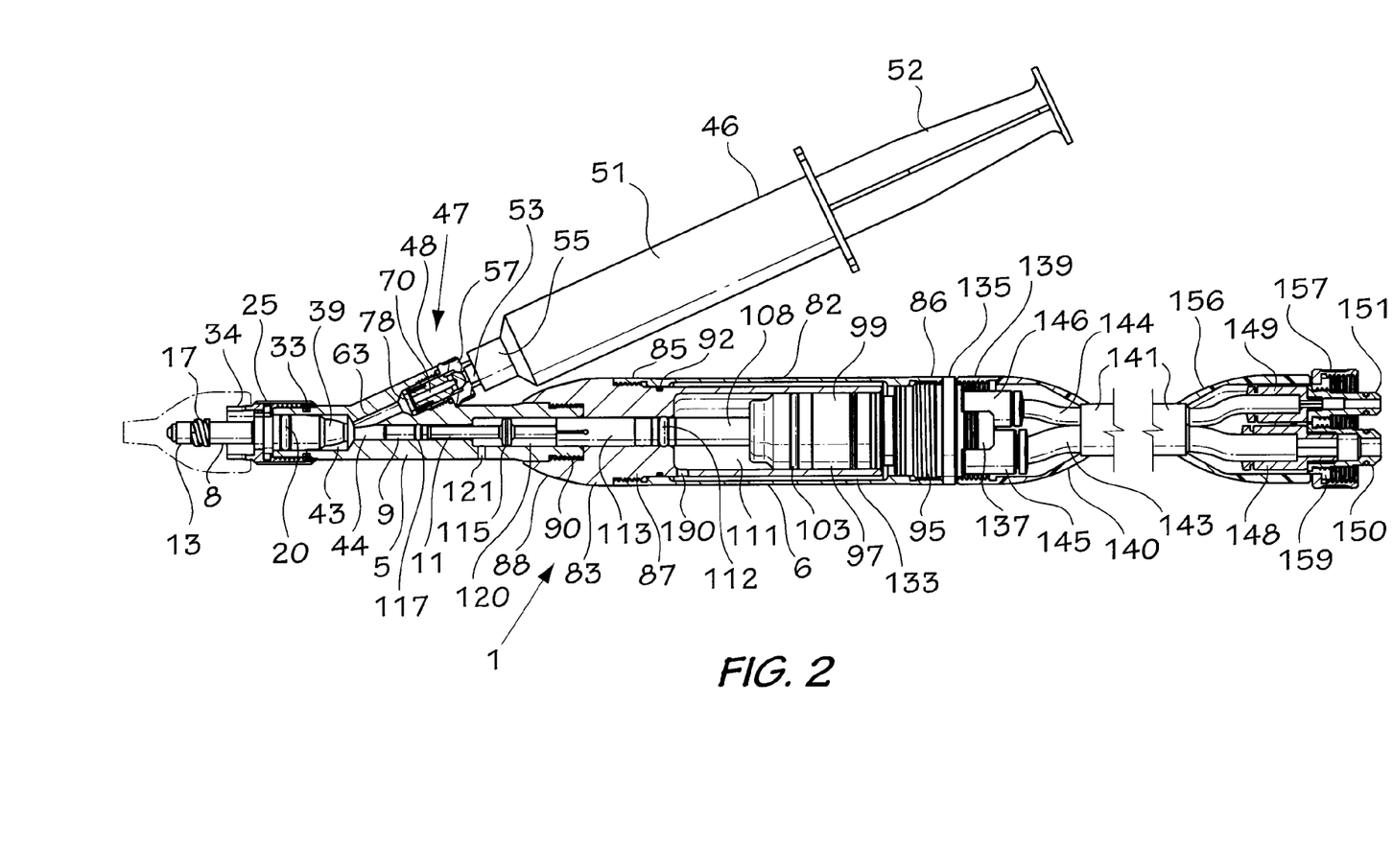
FIG. 2 is a longitudinal sectional view of a wand used in the assembly of FIG. 1.

With reference to FIGS. 1 and 2, the injector assembly of the present invention includes a wand, a control unit and a foot pedal actuator indicated generally at 1, 2 and 3, respectively. The wand 1 includes a tubular barrel defined by front and rear sections 5 and 6, respectively. The front barrel section 5 houses a removable nozzle holder 8 and the front end 9 of a plunger 11.

Figure 3:
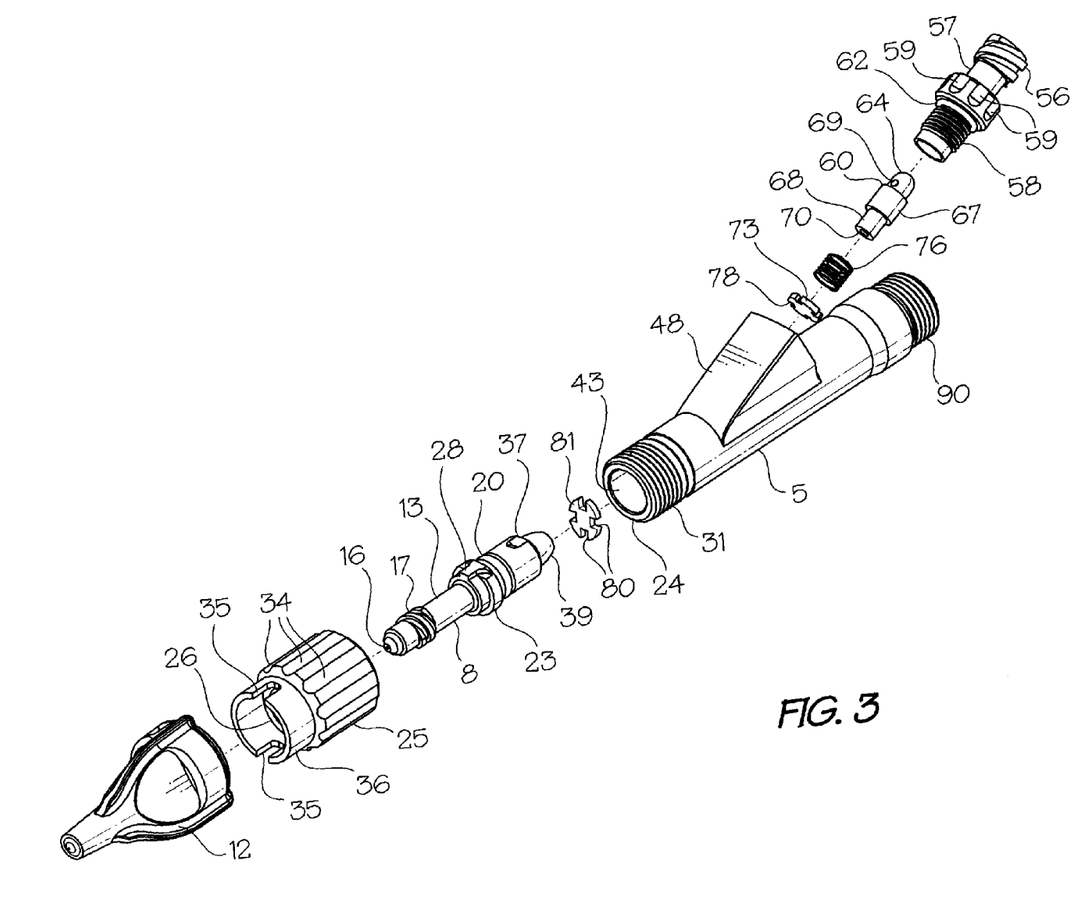
FIG. 3 is an exploded, isometric view of the discharge end of a barrel used in the wand of FIG. 2.
Figure 4:
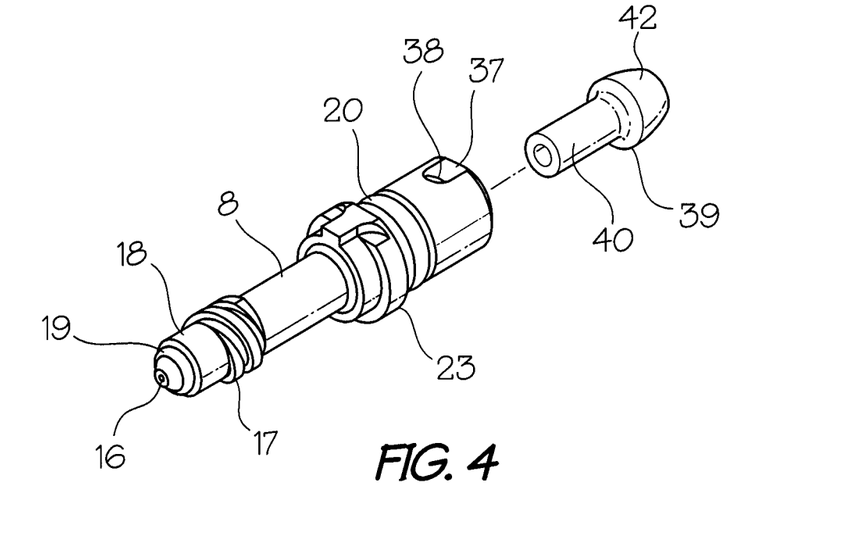
FIG. 4 is an exploded isometric view of a nozzle holder and a valve stem used in the wand of FIG. 2.
Figure 5:
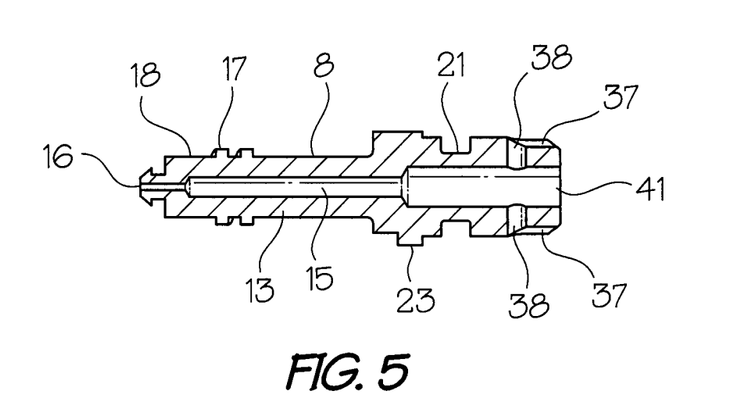
FIG. 5 is a longitudinal sectional view of the nozzle holder of FIG. 4.

The nozzle holder 8 and a disposable nozzle 12 used with the injector are similar to the same elements described in the inventor's U.S. Pat. No. 7,357,781, issued Apr. 15, 2008. As best shown in FIGS. 3 to 5, the nozzle holder 8 includes a tubular body 13 with a passage 15 extending therethrough. Liquid is discharged through a small orifice 16 (FIGS. 3 to 5) in the front end of the body 13. Threads 17 near the outer end 18 of the body 13 are used to connect the disposable nozzle 12 (FIGS. 1 and 3) to the holder. The nozzle 12 is sealed on the holder 8 by an O-ring 19. The body 13 is sealed in the front section 5 of the barrel by an O-ring 20 (FIGS. 2 and 4) which seats in a groove 21 (FIG. 5) near the rear or inner end of the body 13. An annular flange 23 on the body 13 abuts the outer end 24 (FIG. 3) of the barrel section 5 to limit movement of the nozzle holder 8 into the barrel. The nozzle holder 8 is retained in the barrel section 5 by a tubular nut 25 with a radially inwardly extending annular flange 26 therein for engaging the flange 23 on the body 13 of the nozzle holder 8. When assembling the injector, the holder 8 is inserted into the rear end of the nut 25. A small projection 28 on the front of the flange 23 enters a notch 29 in the flange 26 so that the holder 8 cannot rotate in the barrel section 5. Internal threads 30 (FIGS. 7 and 8) on the nut 25 mate with external threads 31 on the outer end 24 of the barrel 5. The nut 25 is sealed with respect to the barrel by O-ring 33 (FIG. 2). Longitudinally extending grooves 34 on the nut 25 facilitate manual mounting of the nut on the barrel section 5.

Figure 7:
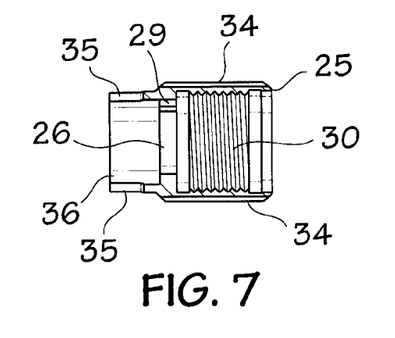
FIG. 7 is a longitudinal sectional view of a nut used on the front or discharge end of the wand of FIG. 2.
Figure 8:
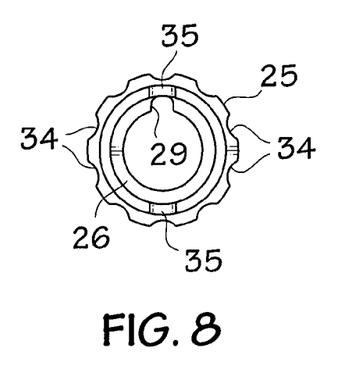
FIG. 8 is a front view of the nut of FIG. 7.

Longitudinally extending notches 35 in the front end 36 of the nut 25 are used to receive a detent (not shown) on the disposable nozzle 12. As described in the above referenced U.S. Pat. No. 7,357,781, the detent extends into one of the notches 35 and is broken off when the nozzle 12 is being removed so that the nozzle cannot be reused.

Figure 6:
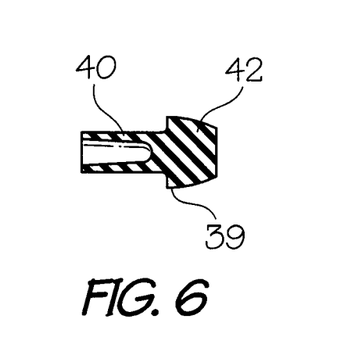
FIG. 6 is a longitudinal sectional view of the valve stem of FIG. 4.

Liquid enters the central passage 15 in the holder body 13 via diametrically opposed grooves 37 in the rear end of the body 13 and radially extending openings 38 connecting the grooves 37 to the passage 15. The inner ends of the openings 38 are normally closed by a rubber valve 39 (FIGS. 2 and 6) which includes a hollow stem 40, which seats in the larger diameter rear end 41 of the passage 15, and a head 42 (FIGS. 4 and 6) which bears against and closes the rear end of the passage 15. When liquid under sufficient pressure enters the openings 38 via the grooves 37, the stem 40 is compressed, whereby the liquid is discharged through the passage 15 and the orifice 16.

When using the nozzle holder described in the above-referenced U.S. Pat. No. 7,357,781, a certain amount of fluid is lost by becoming trapped in an area around a narrow diameter rear end of the holder body. The rear end of the holder 8 of the present invention is essentially the same diameter throughout its length and fills the wide front end 43 (FIG. 2) of a first chamber 44 in the front barrel section 5. Thus, the volume of trapped liquid is reduced.

The chamber 44 is designed to receive a drug or other liquid from a syringe 46. Liquid from the syringe 46 enters the chamber 44 via a one-way valve (FIGS. 1 to 3 and 9) indicated generally at 47 (FIGS. 1 and 2) mounted in a tubular inlet duct 48 defined by an inclined projection on the top of the barrel 5. The syringe 46 is a conventional plastic syringe including a barrel 51 with a plunger 52 slidable in one end thereof for forcing liquid through a narrow diameter nozzle 53 at the other end thereof. The syringe barrel 51 includes a scale (not shown) indicative of the dosage injected each time the injector is operated. A sleeve 55 around the syringe nozzle 53 is internally threaded for attaching the syringe 46 to the threaded top end 56 of a valve body 57 (FIG. 3). The externally threaded bottom end 58 of the valve body 57 is screwed into the inclined inlet duct 48 on the barrel section 5. The middle of the valve body 57 includes grooves 59 which facilitate gripping of the body during insertion into the duct 47.

Figure 9:
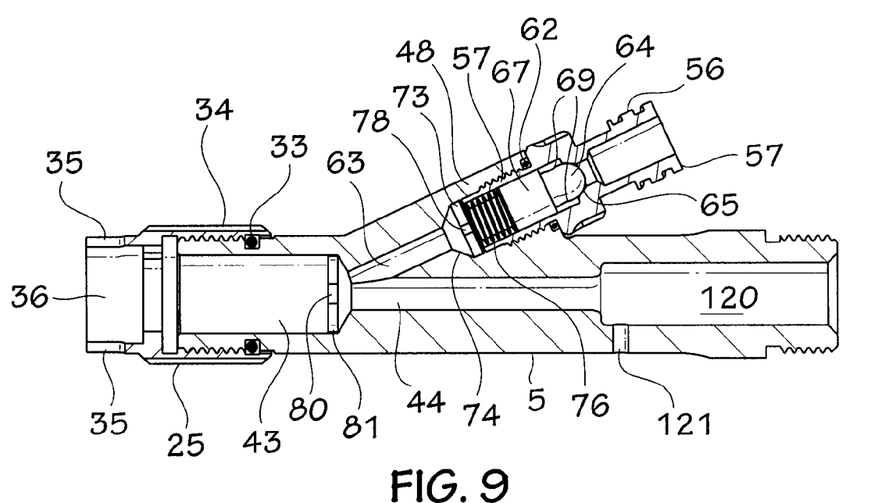
FIG. 9 is a longitudinal sectional view of the front section of the barrel of the wand of FIG. 2.

As best shown in FIGS. 3 and 9, as well as the body 57, the valve 47 includes a piston or stem 60 slidable in body 57. An O-ring 62 seals the valve body 57 in the passage 63 through the inlet duct 48. The valve stem 60 is generally cylindrical with a hemispherical top end 64 (FIG. 8) for seating in a top seat 65 in the body 57, a large diameter centre section 67 for sliding in the inlet duct passage 63 and a smaller diameter bottom end 68, (FIG. 3). Diametrically opposed, radially extending openings 69 in the top end 64 of the stem 60 communicate with a central passage 70 (FIGS. 2 and 3), which has a closed top end and an open bottom end. The open bottom end 68 of the body 57 is maintained slightly spaced apart from a disc-shaped spacer 73 seated on a shoulder 74 in the passage 63 by a helical spring 76. When the syringe plunger 52 moves downwardly, fluid from the syringe 46 flows through the openings 69 and the passage 70 to the bottom of the valve stem 60, through notches 78 in the spacer 73 and then through the remainder of the inlet duct 48 into the chamber 44 in front of the plunger 11 in the barrel 5. During an injection, the spring 76 assisted by fluid pressure in the inlet duct passage 63 closes the valve 47. Following the injection, the helical spring 76 around its bottom end 68 returns the stem 60 to the rest position (FIGS. 2 and 9). Before the first injection, it is necessary to push the syringe plunger 52 downwardly to force fluid through the valve 47 into the chamber 44 in front of the plunger 11. Following a first injection, the plunger 11 is retracted creating a partial vacuum in the chamber 44 which causes the valve 47 to open and liquid from the syringe 46 to be drawn through the inlet duct 48 into the chamber 44. Fluid entering the chamber 44 passes through notches 80 in a spacer 81 into the front end 43 of the chamber.

As best shown in FIGS. 2 and 10 to 12, the rear barrel section 6 includes an elongated tubular body 82 connected to the front barrel section 5 by a tubular plug 83. The body 82 has internally threaded front and rear ends 85 and 86, respectively. The threaded front end 85 receives the plug 83, which has an externally threaded neck 87 and an internally threaded head 88 for receiving the threaded rear end 90 of the front barrel section 5. This structure makes it easy to change the dosage by merely replacing the front barrel section 5 with another section having a larger or smaller chamber 44. The plug 83 is sealed in the body 82 by O-ring 92 (FIG. 2).

Figure 11:
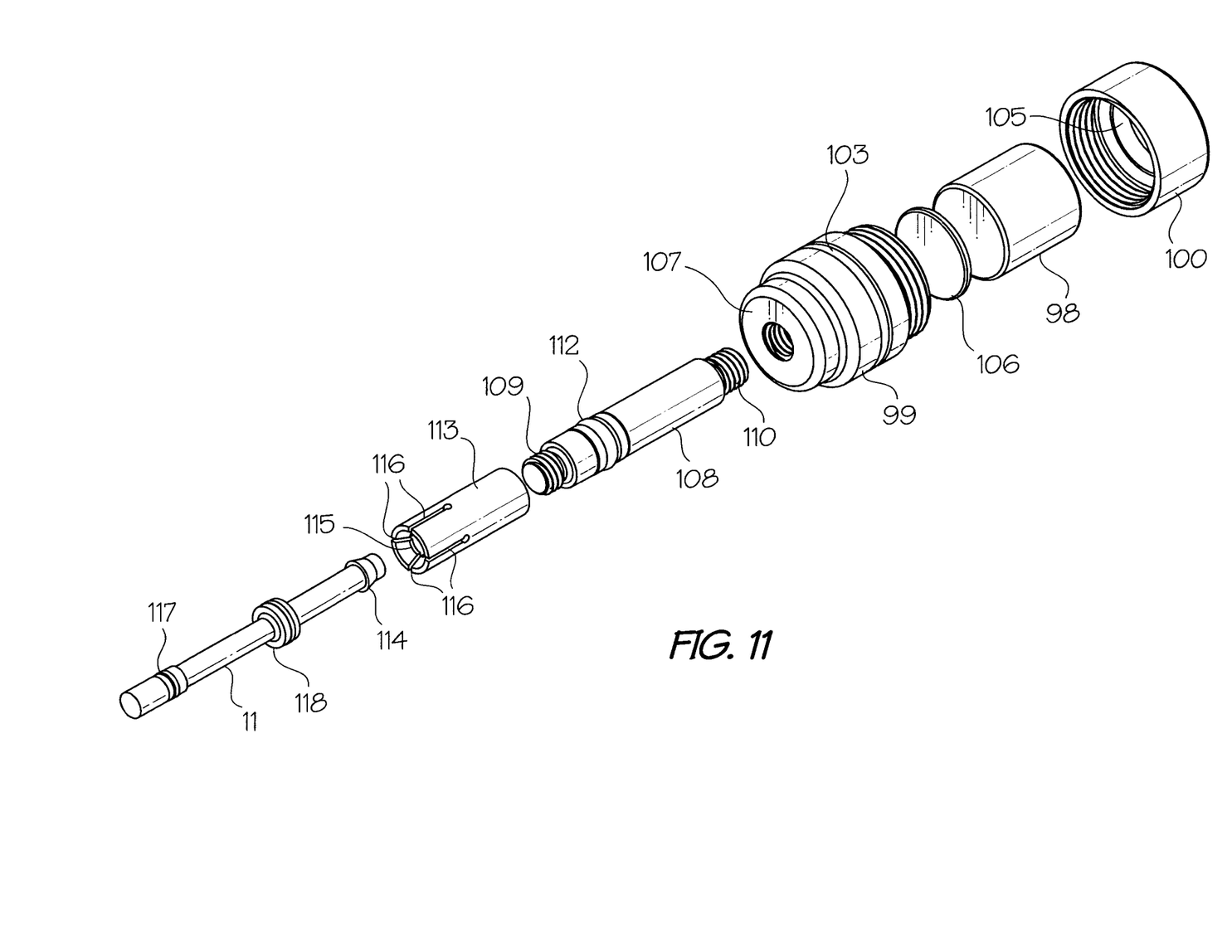
FIG. 11 is an exploded, isometric view of a piston and retractor assemblies used in the injector of FIGS. 1 and 2.
Figure 12:
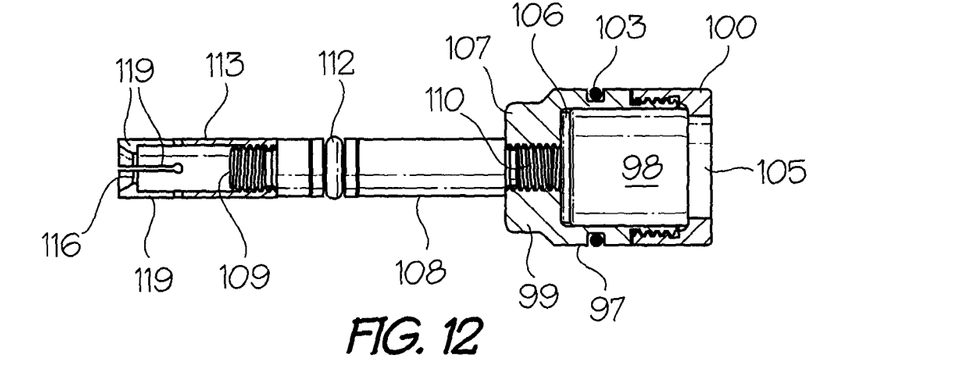
FIG. 12 is a partly sectioned side view of the magnet assembly of FIG. 11.

The rear end 86 of the tubular body 82 is closed by a breach plug 95 through which a gas under pressure flows into and out of the rear end of the barrel assembly. In the rest position, the rear end of a piston assembly 97 abuts the plug 95. Referring to FIGS. 2, 11 and 12, the piston assembly 97, which is slidable in the body 82 includes a cylindrical magnet 98 (FIGS. 11 and 12) mounted in a cup-shaped casing 99, the rear end of which is closed by a nut 100 for maintaining the magnet 98 in the casing. The casing 99 is sealed in the plug 83 by an O-ring 103. In the rest or retracted position of the piston assembly 97, a disc 104 in the front end of the breach plug 95 extends through an opening 105 in the nut 100 into contact with the rear end of the magnet 98 to retain the latter in the retracted position. A disc-shaped spacer 106 is located between the front end of the magnet 98 and the front end 107 of the casing 99 for cushioning the front end of the magnet.

A retractor shaft 108 with threaded front and rear ends 109 and 110, respectively is mounted in the front end 107 of the magnet assembly casing 99. The shaft 108 is slidable in a reduced diameter front end of a second chamber 111 rearwardly of the first chamber 44 in the plug 83 carrying the piston assembly. An O-ring 112 seals the shaft 108 in the plug 83. A retractor sleeve 113 is mounted on the threaded front end 109 of the shaft 108. The sleeve 113 is slidable relative to the plunger 11. During forward movement of the piston assembly 97, the sleeve 113 slides over an annular flange 114 on the rear end of the plunger 11 until the front end 109 of the shaft engages the plunger and drives it forward to expel liquid from the chamber 44. When the piston assembly 97 is retracted, a radially inwardly extending flange 115 in the front end of the sleeve 113 engages the flange 114 on the rear end of the plunger 11 to retract the plunger to the rest position as shown in FIG. 2. The front end of the sleeve 113 includes longitudinally extending slits 116 so that such front end can be flexed to receive the flange 114 on the rear end of the plunger 11. An O-ring 117 (FIGS. 2 and 10) seals the front end 9 of the plunger 11 in the front barrel section 5. An annular flange 118 containing an O-ring 119 is slidable in the large diameter rear end 120 of the passage through the barrel section 5. A hole 121 in the section 5 permits air to enter and escape from the rear end 120 of the passage through the barrel 5 during back and forth movement of the plunger 11.

Figure 10:
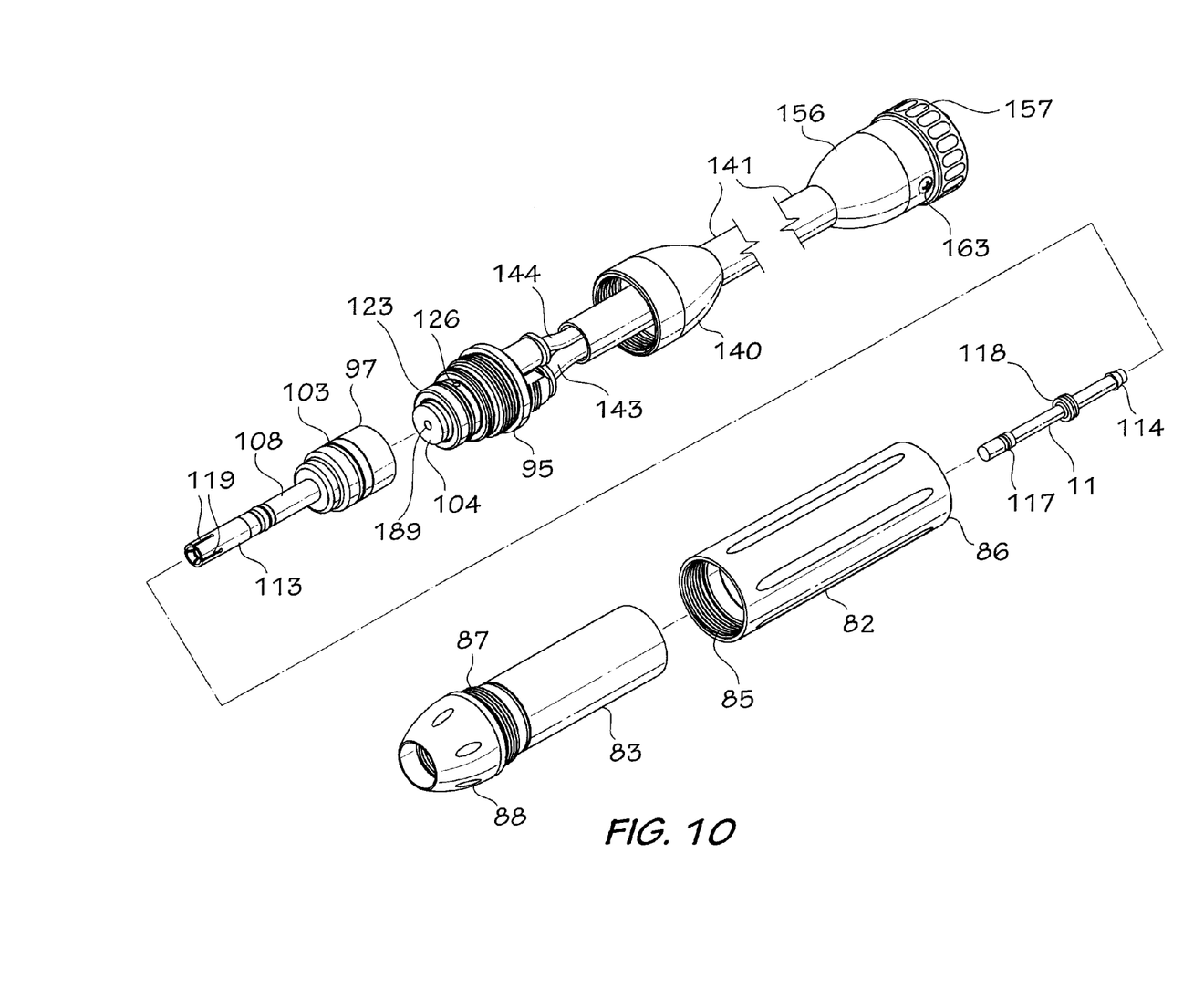
FIG. 10 is an exploded, isometric view of the rear section of the wand barrel and a drive assembly used in the injector of FIGS. 1 and 2.
Figure 13:
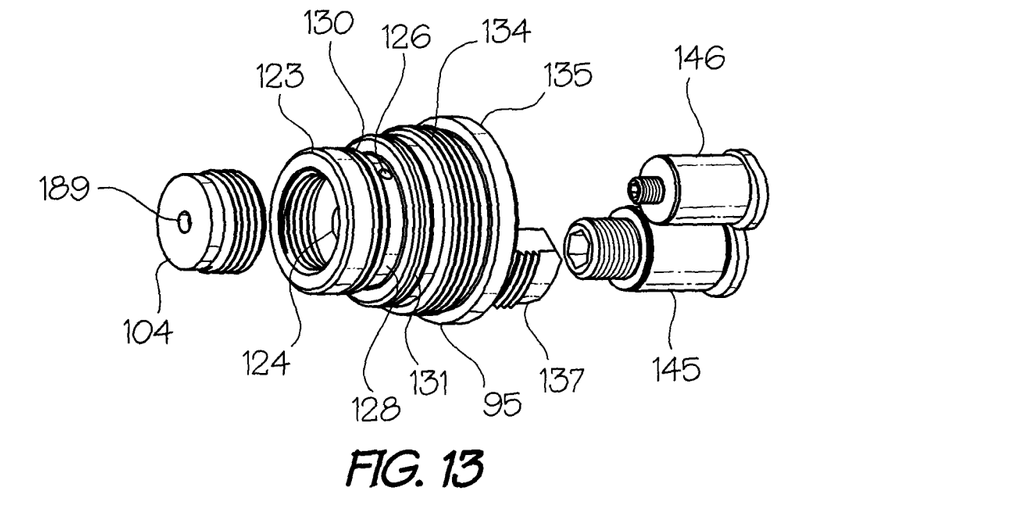
FIG. 13 is an exploded, isometric view of a breach plug used in the wand of FIG. 2.
Figure 14:
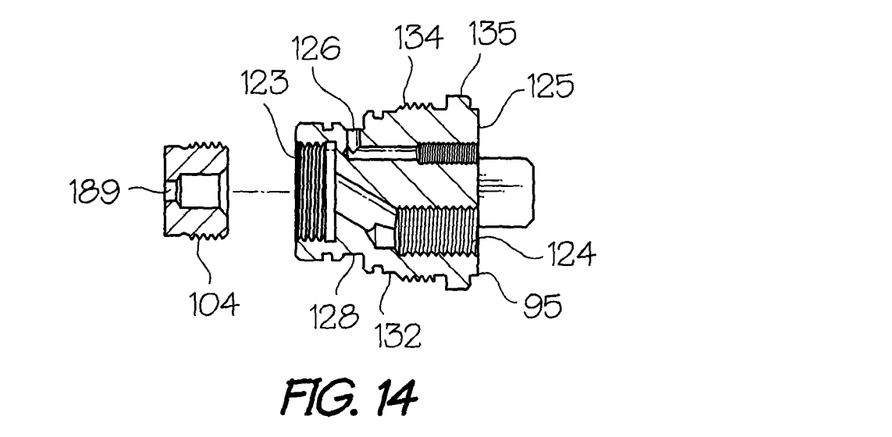
FIG. 14 is an exploded, longitudinal sectional view of the breach plug of FIG. 13.
Figure 15:
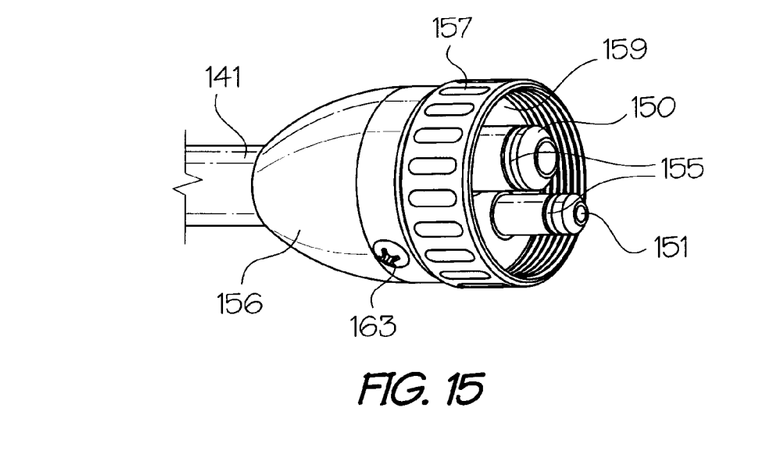
FIG. 15 is an isometric view of one end of a connector assembly for connecting the wand of FIG. 2 to a control unit.
Figure 16:
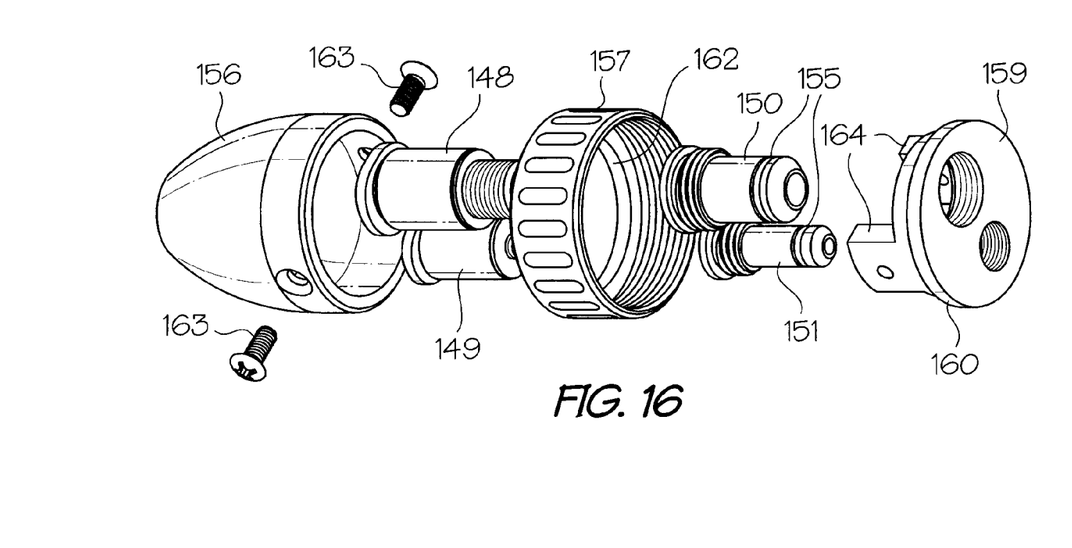
FIG. 16 is an exploded, isometric view of the connector assembly of FIG. 15.

As best shown in FIGS. 10, 13 and 14, the breach plug 95 includes an internally threaded, small diameter front end 123 for receiving the disc 104. A first passage 124 extends longitudinally of the plug 95 from the rear end 125 thereof for carrying gas under pressure to the open internally threaded front end 123 of the plug. A second L-shaped passage 126 extends from the rear end 125 of the plug to an annular groove 128 near the front end 123 of the plug. The groove 128 is separated from the front end 123 by O-rings 130 and 131 in the front end 123 and in the center section 132, respectively. The O-rings 130 and 131 border a passage defined by the tube 82 and the groove 128, whereby gas can flow between the passage 126 in the plug 95 and a cylindrical third chamber 133 surrounding the second chamber (FIG. 2) between the body 82 of the rear barrel section 6 and the plug 83. As shown in FIG. 2, the front end 123 of the breach plug 95 extends into the rear end of the body 82, and is sealed therein by the O-ring 130 (FIG. 13). The center section 132 includes threads 134 (FIGS. 13 and 14) for connecting the plug 95 to the internally threaded rear end 86 of the body 82. An annular flange 135 limits movement of the plug 95 into the rear barrel section 6. A pair of externally threaded ears 137 extend rearwardly from the plug 95 behind the flange 135 for connecting the plug to the internally threaded front end 139 of a cap 140 on one end of a sleeve 141.

Figure 17:
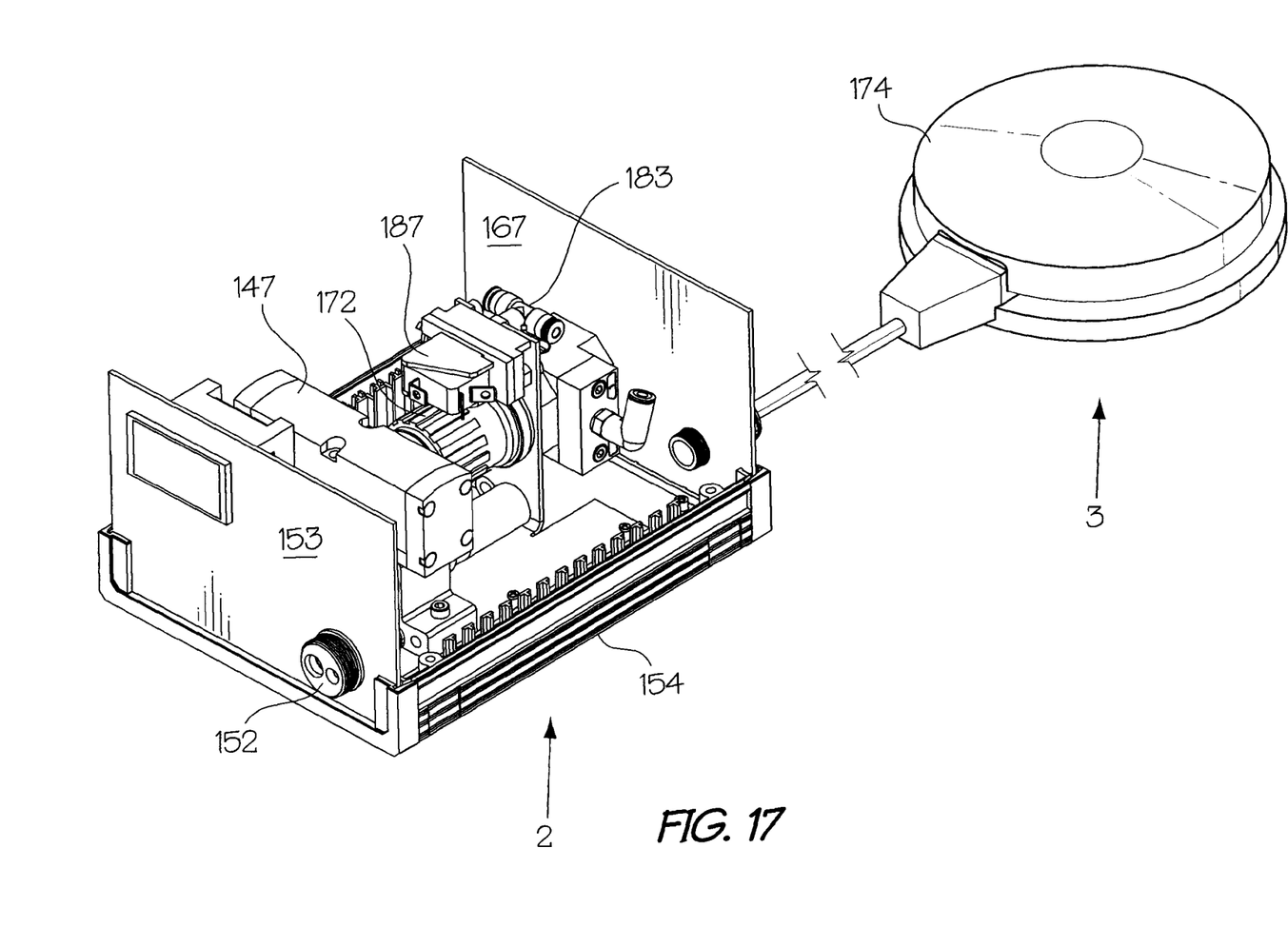
FIG. 17 is an isometric view of the main elements of a pneumatic control system and a foot actuator.

The sleeve 141 contains a pair of tubes 143 and 144, which carry gas under pressure to and from the breach plug 95 via couplers 145 and 146, respectively. Suitable couplers 145 and 146 are so-called push-in fittings available from Festo Inc. of Mississauga, Ontario, Canada. The opposite ends of the tubes 143 and 144 are connected a valve 147 (FIG. 17) in the control unit 2 by push-in couplers 148 and 149, and nipples 150 and 151, respectively, which are plugged into a socket 152 in the front wall 153 of the control unit housing 154. O-rings 155 seal the nipples 150 and 151 in the socket 152. The socket 152 is connected to the valve 147 by tubes (not shown). The couplers 148 and 149 and the nipples 150 and 151 are housed in a sleeve cover 156 and a threaded locking ring 157 which connects the cover to the socket 152 in the front wall 153 of the housing 154 (FIG. 17). The couplers 148 and 149 are threaded into the nipples 150 and 151, and the nipples are screwed into a disc-shaped saddle 159. The saddle 159 is inserted into the cover 156 with the locking ring 157 sandwiched between the saddle and cover. An annular flange 160 on the saddle 159 engages a radially inwardly extending flange 162 in the ring 157. A pair of diametrically opposed screws 163 extend through the cover 156 into ears 164 on the saddle 159 to tie the assembly together. The use of the nipples 150 and 151 with the couplers 148 and 149 makes it relatively easy to connect and disconnect the tubes 143 and 144 from the control unit 2.

Figure 18:
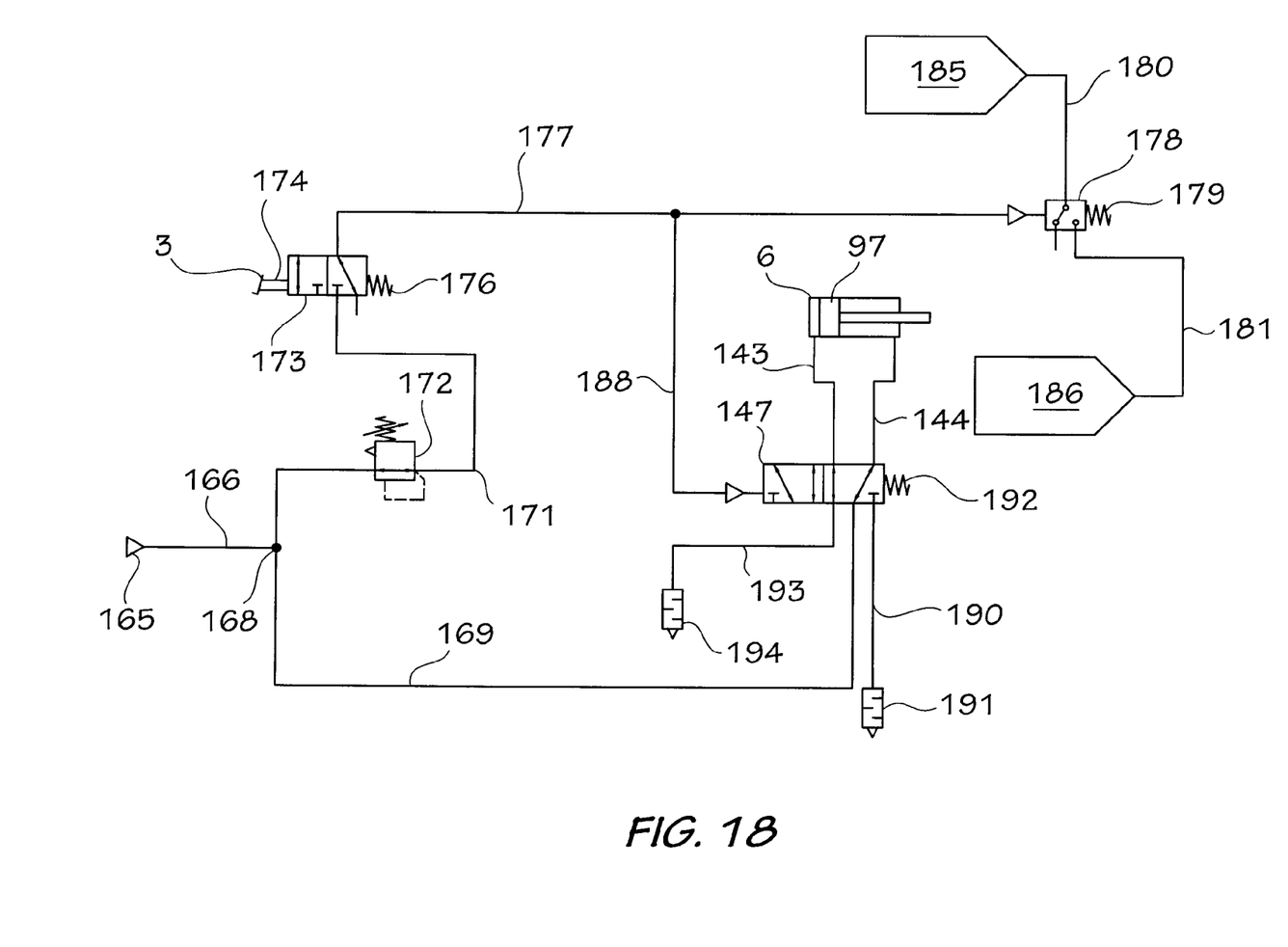
FIG. 18 is a schematic circuit diagram of a pneumatic control system for use with the wand assembly of FIG. 1.

It should be noted that, for the sake of simplicity, elements of the apparatus have been omitted from FIGS. 17 and 18.

Referring to FIGS. 17 and 18, fluid (in this case carbon dioxide) under pressure flows from a source 165 (FIG. 18) thereof through a tube 166 and connectors (not shown) through the rear wall 167 (FIG. 17) of the control unit 2 which forms part of a pneumatic control system. The fluid passes through a T-connector 168 and a line 169 to the valve 147, and through line 171 containing a pressure regulator 172 to the foot actuator 3, which contains a two-way valve 173 operated by a foot pedal 174 with a return spring 176. When the valve 173 is opened by pressing on the foot pedal 174 fluid flows through line 177 to a pressure operated switch 178 with a return spring 179. The switch 178 is connected by lines 180 and 181 and a T-connector 183 (FIG. 17) to terminals 185 and 186 on a counter 187. Each time the switch 178 opens and closes the counter 187 is operated to indicate another injection has been made.

Fluid passing through the foot-operated valve 173 also flows through line 188, providing a pilot signal to the five-way, two position valve 147. The valve 147 opens to a position allowing pressure fluid to flow through the tube 143, the breach plug 95, and a hole 189 (FIGS. 10, 13 and 14) in the disc 104 to the rear end of the piston assembly 97. When sufficient pressure has accumulated, the piston assembly 97 is driven forwardly pushing the plunger 11 to eject the liquid in the chamber 44 through the nozzle holder 8 and the disposable nozzle 12. Simultaneously, gas from in front of the magnet casing 99 is discharged through an opening 190 (FIG. 2) in the rear barrel section body 82 and the chamber 133 between the body 82 and the plug 83. The gas is then discharged through the L-shaped passage 126 in the breach plug 95, the tube 144, the valve 147, a line 190 and a silencer 191.

When the foot pedal 174 is released, the spring 176 closes the valve 173. A spring 192 in the valve 147 moves the valve to the position shown in FIG. 18, i.e. closes the flow of the gas through tube 143 to the rear end of the piston assembly and opens the line 169 to the tube 144. The gas under pressure then flows through the passage 126 in the breach plug 95 and the chamber 133 between the barrel body 82 and the plug 83 into the chamber 111 in front of the magnet casing 99 to drive the piston assembly rearwardly to the rest or start position shown in FIG. 2. Gas behind the piston assembly is expelled via the passage 124 in the breach plug 95, the tube 143, the valve 147, line 193 and a silencer 194.

As mentioned above, when the plunger 11 is retracted by the retractor sleeve 113 on the front end of the piston assembly 97, a partial vacuum is created in the chamber 44 which causes liquid to be drawn from the syringe 46 and through the valve assembly 47 into the chamber 44, making the injector ready for another injection.

The wand assembly can be quite compact. For example, in an existing assembly, the combined length of the wand 1 and the nozzle 12 is approximately 15.3 centimeters, and the outside diameters of the barrel section 5, the barrel section 6 and the nut 25 are approximately 12 mm, 25 mm and 15 mm, respectively.

The invention claimed is:

1. A needleless injector wand assembly comprising
a tubular barrel;
a first chamber at a front, discharge end of said barrel for receiving an injectable liquid from a source thereof;
a nozzle on the front end of said barrel for discharging liquid from the first chamber;
a plunger slidable in the barrel for movement between a retracted position in which liquid is drawn into the first chamber and an extended position in which the liquid is discharged through said nozzle;
a second chamber in said barrel rearwardly of and separated from said first chamber;
a piston slidable in said second chamber for movement under fluid pressure between an extended position in which it moves the plunger to the extended position and a retracted position in which it moves the plunger to a retracted position;
a third chamber in said barrel surrounding said second chamber for alternately receiving gas under pressure from said second chamber during movement of the piston from the retracted to the extended position, and for introducing the gas under pressure to said second chamber during movement of said piston from the extended to the retracted position;
a breach plug closing a rear end of said barrel including a first passage for receiving a gas under pressure from a source thereof, and carrying the gas to a rear end of the piston to cause the piston to move from the retracted to the extended position, and a second passage for carrying the gas under pressure to and from said third chamber to cause said piston to alternately move from the retracted to the extended position and from the extended to the retracted position; and
a pair of tubes connected to a rear end of said breach plug for carrying gas under pressure to and from said breach plug.

2. The wand assembly of claim 1, wherein said piston includes a cylindrical casing with an open rear end slidable in said barrel, and a cylindrical magnet in said casing for abutting a front end of said breach plug in the retracted position of the piston, whereby the piston is retained in the retracted position until subjected to sufficient gas pressure to drive it forwardly against the plunger.

3. The wand assembly of claim 2, including a cover connected to a rear end of said breach plug and covering front ends of said tubes.

4. The wand assembly of claim 1 including a pneumatic control system comprising a first valve connected to the source of gas under pressure for alternately feeding gas under pressure to said first and second passages in said breach plug to cause extension and retraction of the piston; and a foot-operated second valve connected to said source of gas under pressure and to said first valve for opening and closing said first valve to said first and second passages.

5. The wand assembly of claim 1, wherein said tubular barrel includes:
a front section carrying said nozzle on a front end thereof and containing said first chamber and plunger;
a rear section; and
a plug between said front and rear sections, the plug extending into said rear section and having an open rear end for receiving said piston, and the front section being releasably connected to a front end of the plug, whereby the front section can be replaced with another front section having a larger or smaller first chamber.

* * * * *